United States Patent
Stamm et al.

(10) Patent No.: US 10,869,715 B2
(45) Date of Patent: Dec. 22, 2020

(54) DOUBLE BEVEL BLADE TIP PROFILE FOR USE IN CUTTING OF TISSUE

(71) Applicant: COVIDIEN LP, Mansfield, MA (US)

(72) Inventors: Stephen J. Stamm, Wheat Ridge, CO (US); Kim V. Brandt, Loveland, CO (US)

(73) Assignee: Covidien LP, Mansfield, MA (US)

( * ) Notice: Subject to any disclaimer, the term of this patent is extended or adjusted under 35 U.S.C. 154(b) by 629 days.

(21) Appl. No.: 14/564,379

(22) Filed: Dec. 9, 2014

(65) Prior Publication Data
US 2015/0305802 A1 Oct. 29, 2015

Related U.S. Application Data (60) Provisional application No. 61/985,878, filed on Apr. 29, 2014.

(51) Int. Cl.
*A61B 17/3209* (2006.01)
*A61B 18/14* (2006.01)
*A61B 17/00* (2006.01)

(52) U.S. Cl.
CPC ...... *A61B 18/1445* (2013.01); *A61B 17/3209* (2013.01); *A61B 2017/00526* (2013.01); *A61B 2018/1455* (2013.01)

(58) Field of Classification Search
USPC .............................................. 30/346.55, 357
See application file for complete search history.

(56) References Cited

U.S. PATENT DOCUMENTS

| | | | | |
|---|---|---|---|---|
| 3,447,366 A | * | 6/1969 | Villalobos | G01N 3/58 73/104 |
| 3,667,798 A | * | 6/1972 | Rusztowicz | B25B 7/00 294/104 |
| 3,761,372 A | * | 9/1973 | Sastri | B26B 21/54 204/192.15 |

(Continued)

FOREIGN PATENT DOCUMENTS

| | | |
|---|---|---|
| DE | 102004052068 A1 | 4/2006 |
| EP | 1325721 A2 | 7/2003 |

(Continued)

OTHER PUBLICATIONS

European Search Report for Application No. EP14200061 dated Apr. 9, 2015.

(Continued)

*Primary Examiner* — Clark F Dexter (57) ABSTRACT

Methods and devices are described for the design and manufacturing of a knife with a robust double bevel cutting edge profile for use in surgical procedures. The double bevel cutting edge profile may be defined by a combination of a cutting edge angle and a radius of the cutting edge tip. In some embodiments, the cutting edge profile may be defined by a combination of a web thickness profile and a radius of the cutting edge tip. Numerical ranges are identified for each of the various geometric parameters which may define a cutting edge that provides sufficient knife sharpness over many cutting repetitions. In some embodiments a medical device, which implements a knife with a cutting edge, for use in surgical procedures is described.

16 Claims, 8 Drawing Sheets

(56) References Cited

U.S. PATENT DOCUMENTS

| | | | |
|---|---|---|---|
| 3,803,958 A * | 4/1974 | Fernandez-Moran | G01N 1/06 83/15 |
| 3,834,265 A * | 9/1974 | Tafapolsky et al. | A61B 17/3211 83/651 |
| 4,534,827 A * | 8/1985 | Henderson | A61B 17/3211 216/101 |
| 5,120,596 A | 6/1992 | Yamada | |
| 5,234,436 A | 8/1993 | Eaton et al. | |
| 5,376,099 A | 12/1994 | Ellis et al. | |
| 6,099,541 A * | 8/2000 | Klopotek | A61F 9/013 606/166 |
| 6,139,559 A | 10/2000 | Nordan et al. | |
| 6,554,840 B2 | 4/2003 | Matsutani et al. | |
| 6,626,924 B1 * | 9/2003 | Klopotek | A61F 9/013 606/166 |
| 6,811,556 B2 | 11/2004 | Shimmel et al. | |
| 7,105,103 B2 * | 9/2006 | Keenan et al. | A61B 17/32 216/101 |
| 7,135,028 B2 | 11/2006 | Sugimura et al. | |
| 7,396,484 B2 * | 7/2008 | Daskal et al. | A61B 17/3211 216/101 |
| 7,785,485 B2 * | 8/2010 | Daskal et al. | A61B 17/32 216/101 |
| 8,323,301 B2 | 12/2012 | Saito et al. | |
| 2003/0018348 A1 | 1/2003 | Pallikaris et al. | |
| 2003/0074014 A1 | 4/2003 | Castaneda | |
| 2003/0130676 A1 * | 7/2003 | Sugimura et al. | A61F 9/0133 606/166 |
| 2003/0191484 A1 | 10/2003 | Shimmel et al. | |
| 2004/0099120 A1 * | 5/2004 | Yamada et al. | B26B 21/56 83/835 |
| 2004/0143975 A1 * | 7/2004 | Hamada et al. | B26B 21/38 30/346.57 |
| 2004/0220599 A1 | 11/2004 | Pallikaris et al. | |
| 2004/0230210 A1 | 11/2004 | Carriazo | |
| 2005/0188548 A1 * | 9/2005 | Daskal et al. | A61B 17/3211 30/350 |
| 2006/0041266 A1 | 2/2006 | Sullivan et al. | |
| 2006/0058822 A1 | 3/2006 | Rathjen et al. | |
| 2006/0206126 A1 | 9/2006 | Sugimura et al. | |
| 2009/0007436 A1 * | 1/2009 | Daskal et al. | B26B 21/58 30/346 |
| 2009/0012520 A1 | 1/2009 | Hixson et al. | |
| 2009/0198264 A1 * | 8/2009 | Svrluga et al. | A61B 17/3209 606/167 |
| 2010/0024222 A1 * | 2/2010 | Akari et al. | B26B 21/60 30/346.54 |
| 2013/0014395 A1 * | 1/2013 | Patel et al. | B26B 21/60 30/346.54 |
| 2013/0172917 A1 * | 7/2013 | Saito | A61B 17/3211 606/167 |
| 2015/0209067 A1 * | 7/2015 | Stamm et al. | A61B 17/3211 606/174 |
| 2016/0107275 A1 | 4/2016 | Mussio | |

FOREIGN PATENT DOCUMENTS

| | | |
|---|---|---|
| WO | 0168290 A1 | 9/2001 |
| WO | 03066277 A1 | 8/2003 |
| WO | 2006021269 A1 | 3/2006 |

OTHER PUBLICATIONS

Communication pursuant to Article 94(3) EPS for Applicant No. 14200061.1 dated Jul. 11, 2016 from the European Patent Office.

* cited by examiner

FIG. 1

FIG. 2
DETAIL A

FIG. 3A

FIG. 3B
DETAIL B

DOUBLE BEVEL BLADE TIP PROFILE FOR USE IN CUTTING OF TISSUE

CROSS REFERENCE TO RELATED APPLICATION

The present application claims the benefit of and priority to U.S. Provisional Application Ser. No. 61/985,878, filed on Apr. 29, 2014, the entire contents of which are incorporated herein by reference.

BACKGROUND

In certain surgical procedures, a forceps instrument is used which relies on mechanical action between its jaws to grasp, clamp and constrict vessels or tissue. Electrosurgical forceps may utilize both mechanical clamping action and electrical energy to effect hemostasis by heating tissue and blood vessels to coagulate and/or cauterize tissue. Some surgical procedures include more than simply cauterizing tissue, and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately cut the vessel along the newly formed tissue seal. Accordingly, many vessel sealing instruments have been designed that incorporate a knife or blade member which effectively cuts the tissue after forming a tissue seal.

In certain surgical procedures, there may be many repetitions of cauterizing and cutting of tissue. Thus, a surgical knife which is capable of maintaining sufficient sharpness may be valuable. However, due to certain design and manufacturing issues of prior surgical knives, the tip of the knife edge may yield prematurely, thereby rendering the cutting edge too dull to properly cut the tissue.

SUMMARY

Due to the design and manufacturing issues of prior surgical knives, there may be a need for a surgical knife with a robust cutting edge that provides sufficient knife sharpness over many repetitions. Methods and devices are described for the design and manufacturing of a knife with a robust double bevel cutting edge profile for use in surgical procedures. The knife may include a double bevel cutting edge with a cutting edge tip. In some examples, the radius of the cutting edge tip is between 0.000008 inches and 0.000015 inches. The radius of the cutting edge tip may also range between 0.0000092 inches and 0.000014 inches or between 0.00001 inches and 0.000013 inches in some examples. The radius of the cutting edge tip may also be 0.000012 inches in certain embodiments.

The cutting edge may also have a cutting edge angle, which may range between 28 degrees and 36 degrees. The cutting edge angle may also range between 30 degrees and 34 degrees. In certain embodiments, the cutting edge angle is 32 degrees. In some embodiments, the knife may have a length between 7 inches and 16 inches and may have a width between 0.125 inches and 0.5 inches. In certain examples, the knife material has a Rockwell C hardness value between 47 and 53 within a distance from the cutting edge tip of 0.003 inches. The knife may be made from stainless steel or titanium. Additionally, the knife material may be heat treated or coated from a vapor deposition process.

In some embodiments of the invention, a knife has a cutting edge including a cutting edge tip. The radius of the cutting edge tip may range between 0.000008 inches and 0.000015 inches. In certain instances, the cutting edge may include a web thickness profile defined by a web thickness that varies as a function of distance from the tip, where at a distance of 0.003 inches from the tip, the web thickness is between 0.0012 inches and 0.0018 inches. In some embodiments, the knife has a length between 7 inches and 16 inches and has a width between 0.125 inches and 0.5 inches. In certain examples, the knife material has a Rockwell C hardness value between 47 and 53 within a distance from the cutting edge tip of 0.003 inches. The knife may be made from stainless steel or titanium. Additionally, the knife material may be heat treated or coated from a vapor deposition process.

According to various embodiments of the invention, a medical device is provided. The medical device may include a shaft having a distal and a proximal end. In some embodiments, a handle is coupled with the proximal end of the shaft, and the handle includes one or more triggers. The medical device may also include a knife housed within the shaft. In certain examples, the knife includes a cutting edge with a cutting edge tip and a cutting edge angle. The radius of the tip may range between 0.000008 inches and 0.000015 inches and the cutting edge angle may range between 28 degrees and 36 degrees. The knife may be configured to deploy and retract from the distal end of the shaft in response to an actuation of at least one of the one or more triggers.

In some embodiments, the medical device includes a pair of jaws coupled with the distal end of the shaft. The pair of jaws may be configured to hinge open and closed in response to an actuation of at least one of the one or more triggers. In some embodiments of the medical device, the knife may have a length between 7 inches and 16 inches and may have a width between 0.125 inches and 0.5 inches. In certain examples, the knife material has a Rockwell C hardness value between 47 and 53 within a distance from the cutting edge tip of 0.003 inches. The knife may be made from stainless steel or titanium. Additionally, the knife material may be heat treated or coated from a vapor deposition process.

Methods for making a knife for cutting tissue are provided according to certain embodiments of the invention. For example a method for forming a cutting edge angle of a knife between 28 degrees and 36 degrees is provided. The method may also include forming a radius of a tip of the knife between 0.000008 inches and 0.000015 inches. In some examples, the method for forming the cutting edge angle between 28 degrees and 36 degrees may include a grinding process. Other examples of methods for forming the cutting edge between 28 degrees and 36 degrees may include a stamping process. In certain instances, an electro polishing process may be used to form the radius of the tip between 0.000008 inches and 0.000015 inches.

In another example of a method for making a knife according to embodiments of the invention, a knife tip is formed with a radius between 0.000008 inches and 0.000015 inches. The method may further include forming a web thickness profile of a cutting edge of the knife where the web thickness profile may be defined by a web thickness that varies as a function of distance from the tip. In some embodiments, the web thickness is between 0.0012 inches and 0.0018 inches at a distance of 0.003 inches from the tip. The web thickness profile may be formed by a grinding process, for example. In some embodiments, a stamping process may be utilized to form the web thickness profile. In yet other instances, a photolithography process may be utilized to form the web thickness profile of the cutting edge and the radius of the tip between 0.000008 inches and 0.000015 inches. The radius of the tip may be formed between 0.000008 inches and 0.000015 inches by utilizing an electro polishing process in some examples.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures may be provided for the purpose of illustration and description only, and not as a definition of the limits of the claims.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Methods and devices are described for the design and manufacturing of a knife with a robust double bevel cutting edge profile for use in surgical procedures. The cutting edge of a knife may be defined by various combinations of geometric parameters and relationships. For example, the cutting edge may be defined by a cutting edge angle and a cutting edge tip radius. In other examples, the cutting edge may be defined by a web thickness profile and a cutting edge tip radius. Numerical ranges are identified for each of the various geometric parameters which define a cutting edge that provides sufficient knife sharpness over many cutting repetitions. Additionally, various methods for forming the geometric parameters of the cutting edge of a knife within certain numerical ranges are provided.

Figure 1:
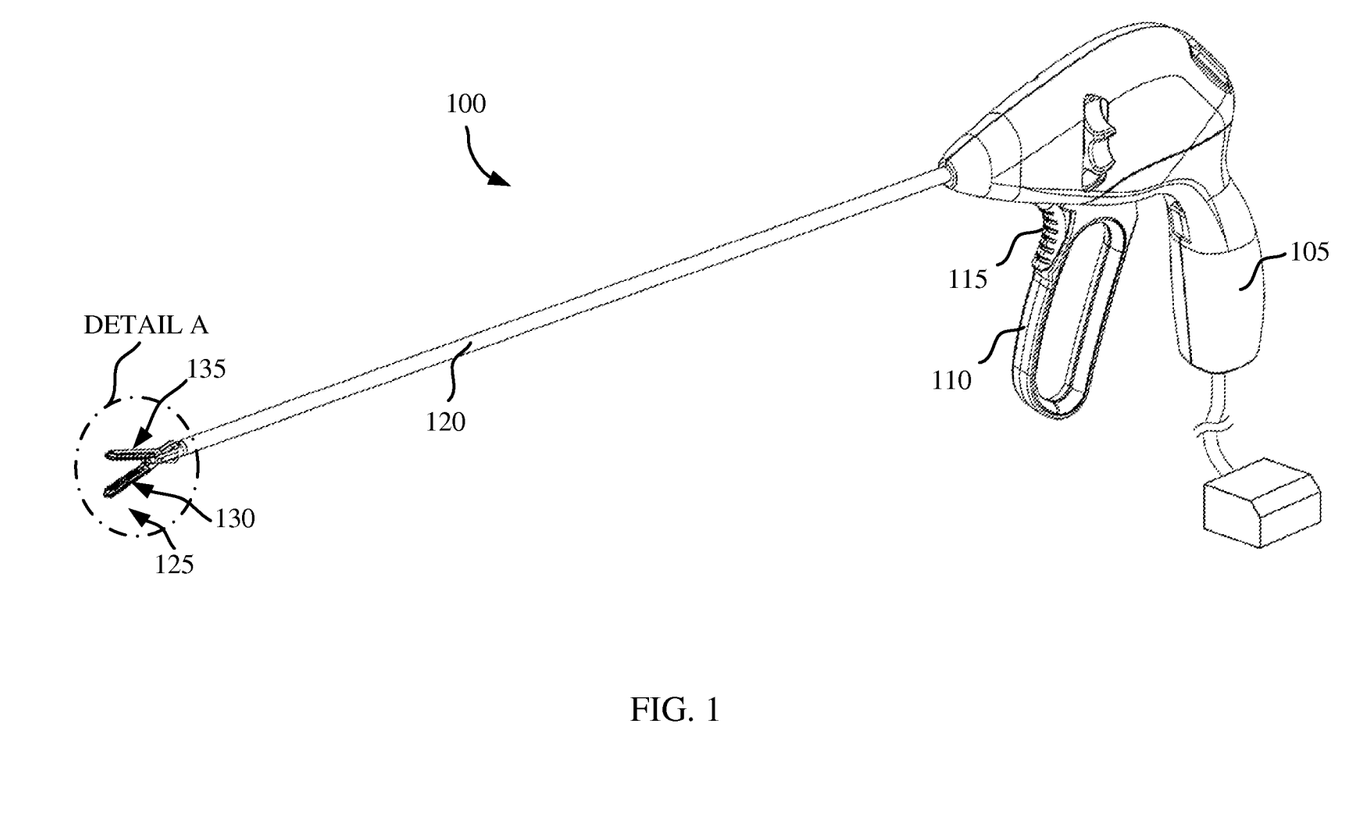
FIG. 1 is a side, perspective view of a forceps provided in accordance with the present disclosure.

With reference to FIG. 1, an example of an electrosurgical forceps 100 device is shown. The forceps 100 are configured for use in various surgical procedures, and include a handle 105, a shaft 120, a first trigger 110, a second trigger 115, a jaw assembly 125, and a knife (not shown) that mutually cooperate to grasp, treat, and divide tubular vessels and vascular tissues. The jaw assembly 125 is coupled with the shaft 120 and includes jaws 130, 135. In some embodiments, one of jaws 130, 135 is configured to pivot about pivot pin (not shown) in response to an actuation of trigger 110, whereas the other jaw is configured to remain stationary. Such a configuration is termed unilateral pivoting. In other examples, configured for bilateral pivoting, each of jaws 130, 135 is configured to pivot about a pivot pin in response to an actuation of trigger 110.

A knife (not shown) is associated with the jaw assembly 125 and the shaft 120, and is configured to extend and retract from the distal end of shaft 120 in response to an actuation of trigger 115. The knife may have any length and width suitable for use in surgical procedures. In some embodiments, the knife may have a length of between 7 inches and 16 inches and may have a width of between 0.125 inches and 0.5 inches. The distal end of the knife may include a double bevel cutting edge, which may be defined by a combination of a cutting edge angle and a radius of the cutting edge tip. In such examples, the cutting edge angle may range between 28 degrees and 36 degrees and the radius of the cutting edge tip may range between 0.000008 inches and 0.000015 inches. In some embodiments, the cutting edge may be defined by a combination of a web thickness profile and a radius of the cutting edge tip. In such examples, the radius of the cutting edge tip may range between 0.000008 inches and 0.000015 inches, and at a distance of 0.003 inches from the tip, the web thickness may range between 0.0012 inches and 0.0018 inches. Each of the geometric parameters related to the knife and the cutting edge of the knife will be discussed in greater detail below.

Figure 2:
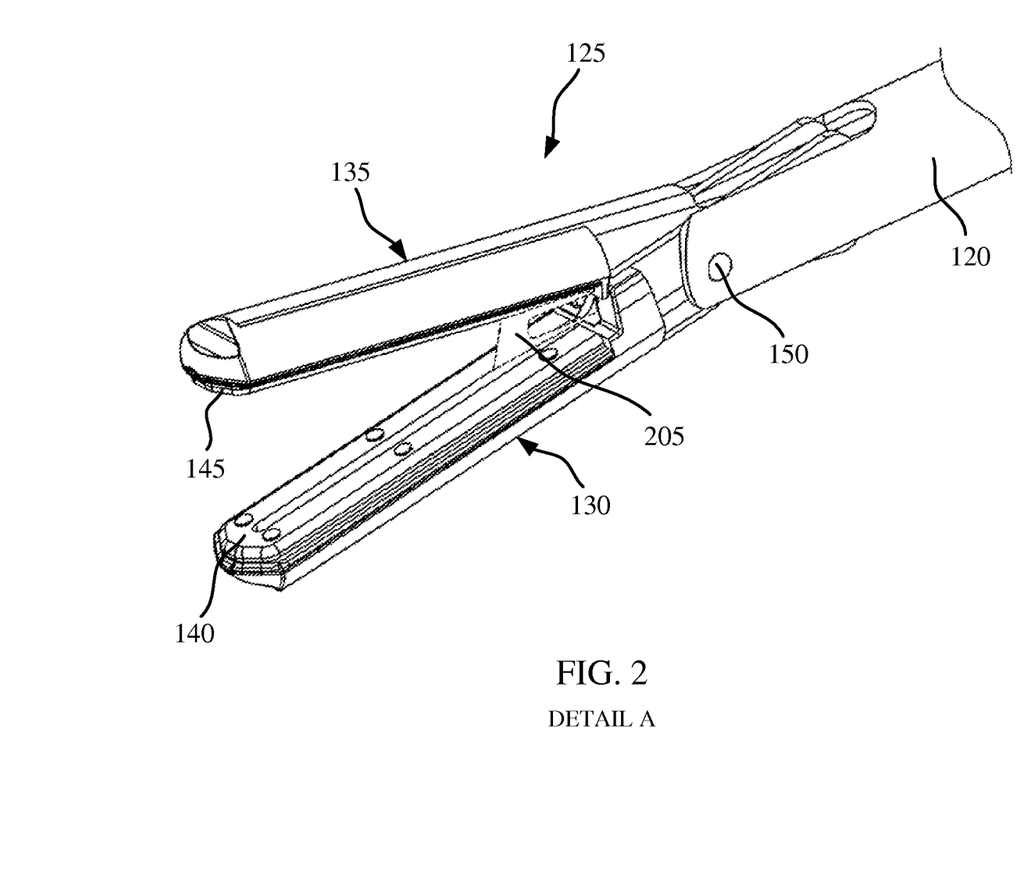
FIG. 2 is a side, perspective view of a distal end of the forceps of FIG. 1 wherein jaw members of the forceps are disposed in a spaced-apart position.

FIG. 2 is a detailed view of jaw assembly 125 of FIG. 1 showing the jaw assembly 125 in an open position. Jaws 130, 135 may be configured to pivot about pivot pin 150 in response to an actuation of trigger 110 shown in FIG. 1. Jaw assembly 125 may include an electrically conductive sealing plate 140, 145 which is electrically coupled with a power source (not shown) to deliver electrical energy, such as RF energy, to effect hemostasis by heating tissue and blood vessels to coagulate and/or cauterize tissue grasped between the jaws 130, 135. The power source may be external, or in some embodiments, may be internal such as a battery for example. FIG. 2 shows knife 205, which may be an example of the knife described in connection with FIG. 1. The knife 205 may be associated with the shaft 120 and the jaws 130, 135 and may be configured to extend and retract from the distal end of shaft 120 in response to an actuation of trigger 115 to cut the cauterized tissue. In certain circumstances, the knife 205 may need to cut tissue grasped between jaws 130, 135 that has not been treated by RF energy. Untreated tissue is tougher than treated tissue, and therefore requires a sharper and more robust cutting edge to accurately cut the tissue. According to various embodiments of the invention, a robust cutting edge of a knife may be defined by a combination of a cutting edge angle, a web thickness profile, and/or a radius of the cutting edge tip, as described in more detail above and below.

Figure 3A:
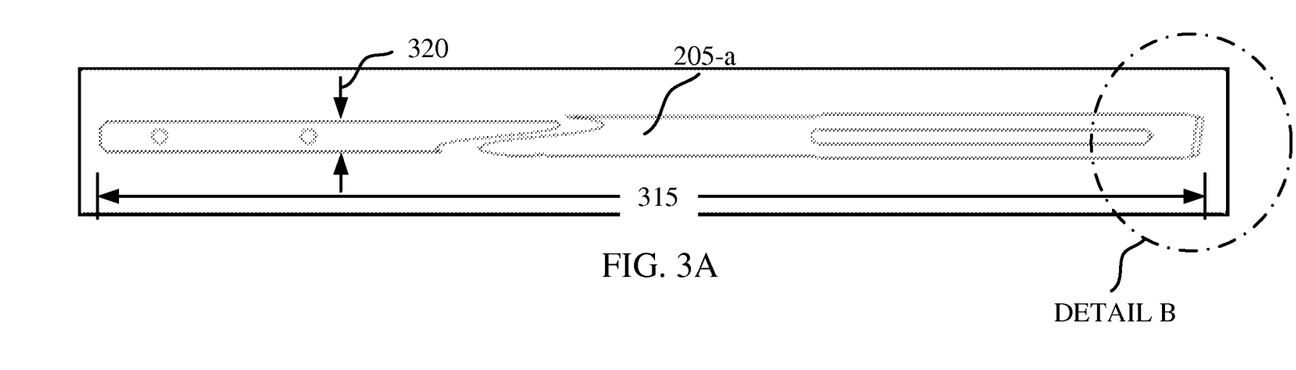
FIG. 3A is a side view of a knife in accordance with the present disclosure.
Figure 3B:
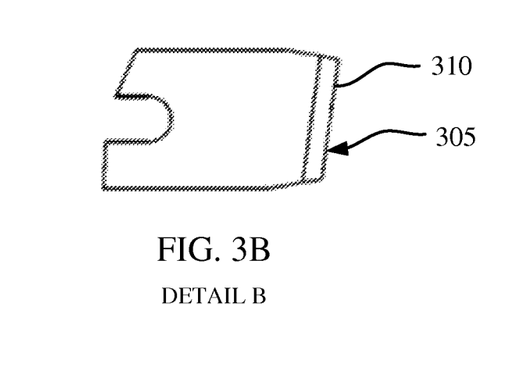
FIG. 3B is a detail view of the distal end of the knife of FIG. 3A.

FIG. 3A shows an example of a knife 205-a according to various aspects of the invention, which may be an example of knife 205 from FIG. 1 or FIG. 2. In the illustrated example, the knife 205-a has a knife length 315, which in some examples may range between 7 inches and 16 inches. Knife 205-a also has a knife width 320, which in some examples may range between 0.125 inches and 0.5 inches. In certain examples, the knife width 320 may be approximately 0.25 inches. FIG. 3B illustrates an example of a detailed view of the distal end of knife 205-a showing the double bevel cutting edge 305 and cutting edge tip 310 of knife 205-a. As will be discussed in more detail, the cutting edge 305 may be defined by a combination of a cutting edge angle and a radius of the cutting edge tip. In some embodiments, the cutting edge angle may range between 28 degrees and 36 degrees and the radius of the cutting edge tip may range between 0.000008 inches and 0.000015 inches. In other examples, the cutting edge 305 may be defined by a combination of a web thickness profile and a radius of the cutting edge tip. In such examples, the radius of the cutting edge tip may range between 0.000008 inches and 0.000015 inches, and at a distance of 0.003 inches from the tip, the web thickness may range between 0.0012 inches and 0.0018 inches.

Knife 205-a may be manufactured from various metallic materials such as stainless steel or titanium. However, it will be appreciated to those skilled in the art that other biocompatible materials may also be used, such as silicone-based materials. In some embodiments, a material with a Rockwell C hardness value of greater than approximately 47 is used. In some examples, the Rockwell C hardness value of the knife material may range between approximately 47 and 52. As will be discussed in more detail below, depending on the process used to fabricate the knife 205-a, the knife material may have a Rockwell C hardness value of between approximately 47 and 53 either before or after the manufacturing process.

Figure 4:
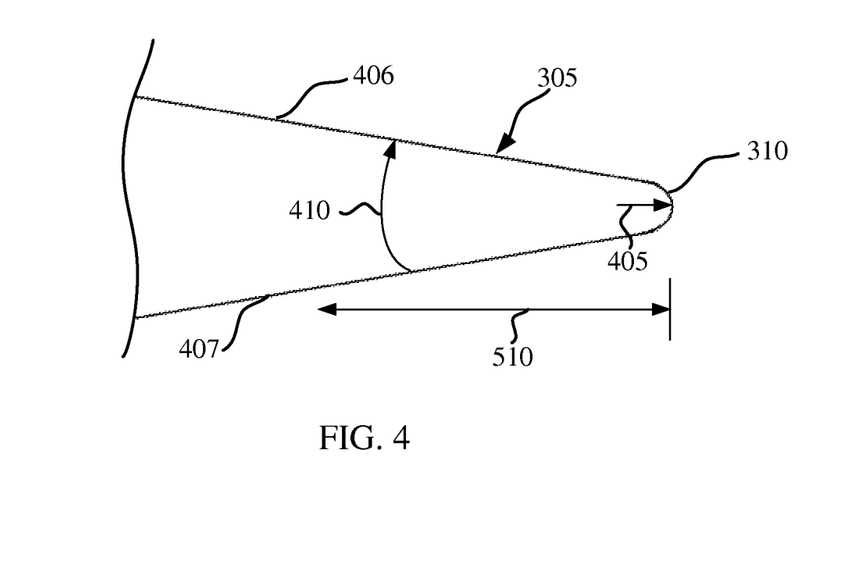
FIG. 4 is a schematic view of a cutting edge profile of a knife in accordance with certain embodiments of the present disclosure.

FIG. 4 shows a cross-sectional view illustrating an example of the double bevel cutting edge 305 of a knife. The cutting edge 305 may be an example of the cutting edge 305 of knife 205 from any of FIG. 1, FIG. 2, or FIG. 3. The cutting edge 305 may include the cutting edge tip 310. The shape and size of the cutting edge tip may affect the sharpness and robustness of the cutting edge 305. In some embodiments of the invention, the tip 310 may be rounded and may be defined by a cutting edge tip radius 405. As described in detail below, the cutting edge tip radius 405 may be precisely measured and controlled through various manufacturing processes. For example, the cutting edge tip 310 may be formed with a cutting edge tip radius 405 between 0.000008 inches and 0.000015 inches. Other ranges for the cutting edge tip radius 405 may be suitable for maintaining a sharp and robust cutting edge 305. For example, the cutting edge tip radius 405 may be between 0.0000092 inches and 0.000014 inches. In other examples, the cutting edge tip radius 405 may be between 0.00001 inches and 0.000013. In yet other embodiments, the cutting edge tip radius 405 may be 0.000012 inches. Controlling the shape and size of the cutting edge tip radius 405 may prevent premature dulling by removing cutting edge tip non-uniformities, such as a burr.

The cutting edge 305 may also include a cutting edge angle 410, which may be defined as the angle measured between a bottom bevel surface 407 and a top bevel surface 406 of the cutting edge 305. The value of the cutting edge angle 410 may affect the sharpness and robustness of the cutting edge 305. For example, a cutting edge 305 with a lower cutting edge angle 410 may be sharper than a cutting edge 305 with a higher cutting edge angle 410. However, a lower cutting edge angle 410 may also result in a cutting edge 305 with less strength and robustness than a cutting edge 305 with a higher cutting edge angle 410. As described in detail below, the cutting edge angle 410 may be precisely measured and controlled through various manufacturing processes. In some embodiments of the invention, the cutting edge angle 410 may range between 28 degrees and 36 degrees. In other examples of the invention, the cutting edge angle 410 may range between 30 degrees and 34 degrees. In yet other embodiments, the cutting edge angle 410 may be 32 degrees.

A length measurement starting at the cutting edge tip 310 and extending longitudinally from the cutting edge tip 310 may be defined as a distance 510 from the cutting edge tip 310. In certain embodiments, the cutting edge angle 410 may be a constant value for all distances 510 from the cutting edge tip 310. Alternatively, the cutting edge 305 may include two or more portions, each with a different cutting edge angle 410. For example, within a distance 510 from the cutting edge tip 310 of approximately 0.003 inches, the cutting edge angle 410 may be between 28 degrees and 36 degrees. However, for distances 510 from the cutting edge tip 310 of greater than approximately 0.003 inches, the cutting edge angle 410 may be greater than 36 degrees or less than 28 degrees.

The values of the cutting edge angle 410 and the cutting edge tip radius 405 may be varied independently of one another to form various cutting edge profiles. As used herein, a cutting edge profile may refer to a particular combination of all the geometric parameters that define the cutting edge 305. Accordingly, a cutting edge profile of cutting edge 305 may be defined by the combination of a particular cutting edge tip radius 405 and a particular cutting edge angle 410. For example, a cutting edge profile may be defined by a cutting edge 305 with a cutting edge tip radius 405 equal to 0.000008 inches and a cutting edge angle 410 equal to 28 degrees. Another example of a cutting edge profile may be defined by a cutting edge 305 with a cutting edge tip radius 405 equal to 0.000015 inches and a cutting edge angle 410 equal to 36 degrees. Yet another example of a cutting edge profile may be defined by a cutting edge 305 with a cutting edge tip radius 405 equal to 0.000012 inches and a cutting edge angle 410 equal to 32 degrees. By varying the cutting edge angle 410 and the cutting edge tip radius 405 within the ranges discussed above, a variety of cutting edge profiles may be defined that provide adequate sharpness to cut a wide variety of treated and/or untreated tissue while also providing sufficient strength to withstand yielding of the cutting edge.

The cutting edge profiles described herein are not limited to knives such as knife 205. Instead, the cutting edge profiles may be implemented with various types of surgical knives having a variety of shapes and sizes. Additionally, the cutting edge profiles may be used with knives that are compatible with various types of medical or surgical devices other than the electrosurgical forceps 100. Furthermore, the cutting edge profiles may be implemented with freestanding surgical knives that do not require a medical device assembly. Additionally, the cutting edge profiles may be used with knifes with other applications other than surgery such as shaving, for example.

Figure 5A:
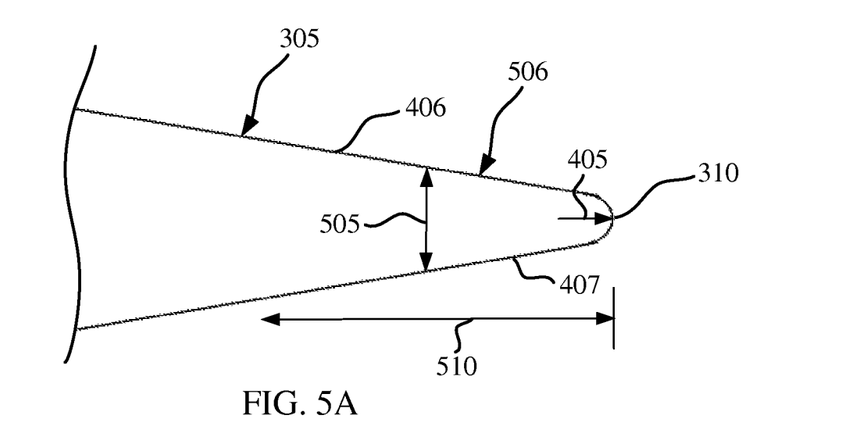
FIG. 5A is a schematic view of a cutting edge profile of a knife in accordance with certain embodiments of the present disclosure.
Figure 5B:
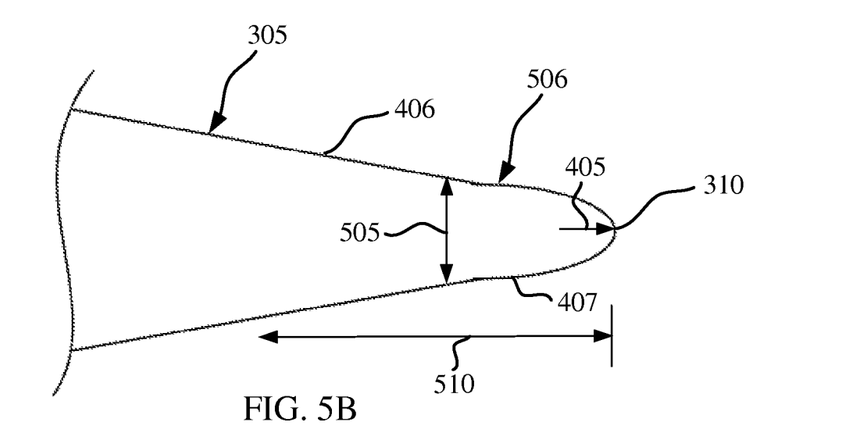
FIG. 5B is a schematic view of a cutting edge profile of a knife in accordance with certain embodiments of the present disclosure.
Figure 5C:
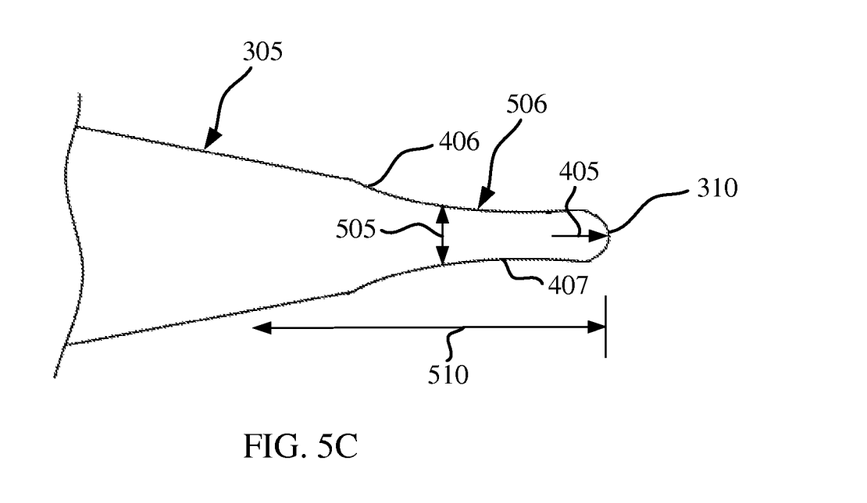
FIG. 5C is a schematic view of a cutting edge profile of a knife in accordance with certain embodiments of the present disclosure.

FIGS. 5A-5C show cross-sectional views illustrating examples of various embodiments of a double bevel cutting edge 305 of a knife. Cutting edge 305 may be an example of the cutting edge 305 of knife 205 from any of FIG. 1, FIG. 2, FIG. 3 or FIG. 4. A thickness measurement between the bottom surface 407 and the top surface 406 may be defined as a web thickness 505. Furthermore, a web thickness profile 506 may be defined by the web thickness 505 as a function of the distance 510 from the cutting edge tip 310. The web thickness profile may affect the sharpness and robustness of the cutting edge 305. According to various embodiments of the invention, at a distance 510 from the cutting edge tip 310 equal to approximately 0.003 inches, the web thickness 505 is between 0.0012 inches and 0.0018 inches. From the cutting edge tip 310 up to a distance 510 from the cutting edge tip 310 of approximately 0.003 inches, the shape of the web thickness profile 506 may vary. For example, referring to FIG. 5A, the web thickness profile 506 may be defined by a linear increase in web thickness 505 as the distance 510 from the cutting edge tip 310 increases. In some embodiments, the web thickness profile 506 may vary non-linearly as the distance 510 from the cutting edge tip 310 increases. For example, as shown in FIG. 5B, the web thickness profile 506 may be defined as a convex or generally outwardly-bulging shape. In yet another embodiment, as shown for example in FIG. 5C, the web thickness profile 506 may be defined as a concave or generally inwardly-curved shape. As discussed in detail below, the shape of the web thickness profile 506 may depend on the manufacturing process used to form the cutting edge 305.

According to various embodiments of the invention, a cutting edge profile may be defined by a combination of a web thickness profile 506 and a cutting edge tip radius 405. For example, a cutting edge profile may be defined by a cutting edge tip radius 405 between 0.000008 inches and 0.000015 inches and a web thickness profile 506 according to FIG. 5A, where at a distance 510 from the cutting edge tip 310 of approximately 0.003 inches, the web thickness 505 is between 0.0012 inches and 0.0018 inches. In some examples, the web thickness 505 may be greater than 0.0018 inches at a distance 510 from the cutting edge tip 310. In other examples, a cutting edge profile may be defined by a web thickness profile 506 according to FIG. 5B or FIG. 5C, where at a distance 510 from the cutting edge tip 310 of approximately 0.003 inches, the web thickness 505 is between 0.0012 inches and 0.0018 inches, and the cutting edge tip radius 405 is between 0.000008 inches and 0.000015 inches. By varying the web thickness profile 506 and the cutting edge tip radius 405 within the ranges discussed above, a variety of cutting edge profiles may be defined that provide adequate sharpness to cut a wide variety of treated and/or untreated tissue while also providing sufficient strength to withstand yielding of the cutting edge.

Figure 6:
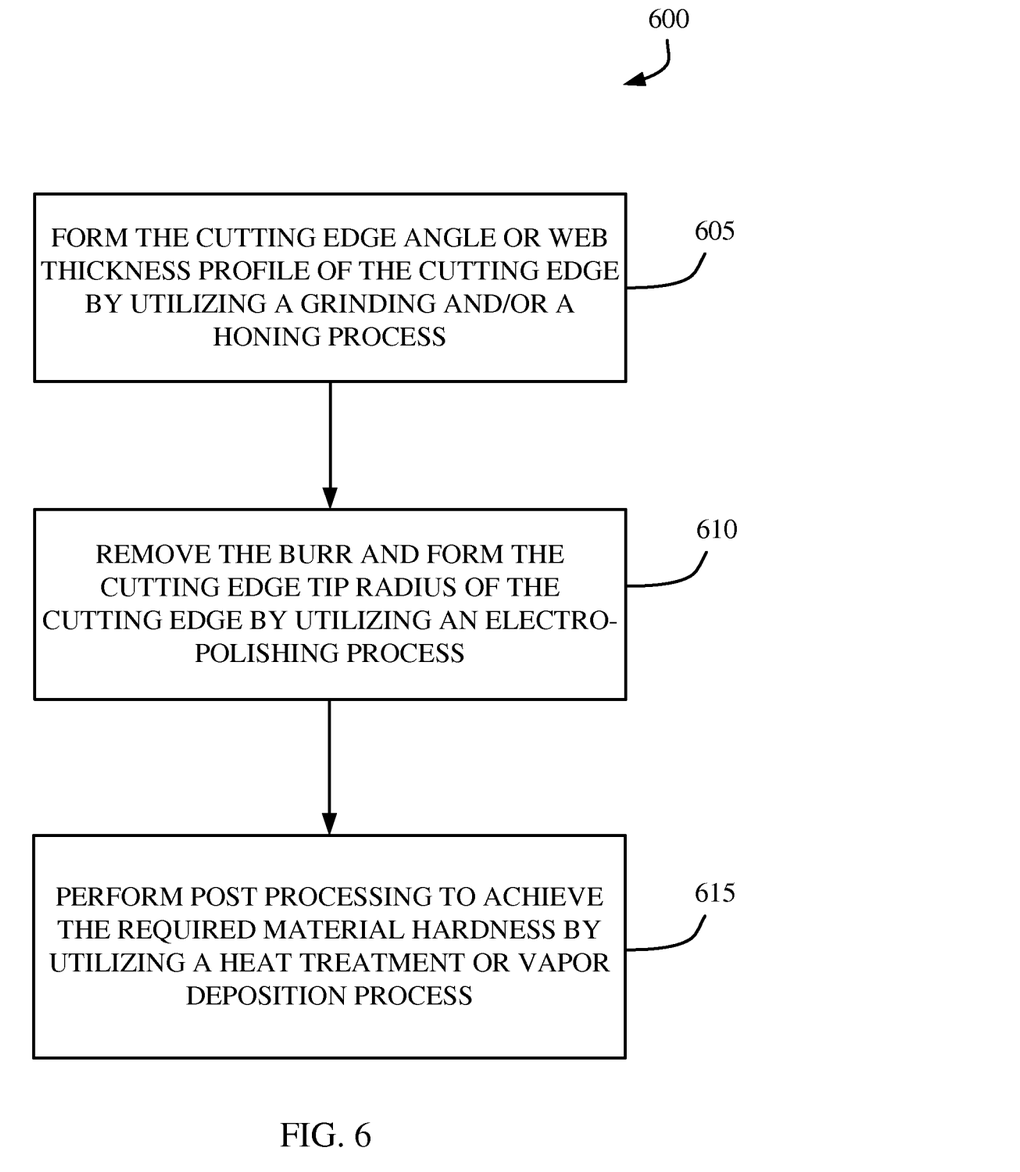
FIG. 6 is a flowchart of a method for forming a surgical knife in accordance with certain embodiments of the present disclosure.

The novel cutting edge profiles described in connection with FIG. 1 to FIG. 5 may be formed using a variety of manufacturing techniques. In some examples, the entire cutting edge profile may be formed from a single manufacturing process. In other instances, the cutting edge profile may be formed by a combination of manufacturing processes. According to various embodiments of the invention, a manufacturing process may be utilized to form the cutting edge angle 410 between 28 degrees and 36 degrees. In other embodiments, a manufacturing process may be utilized to form a web thickness profile 506 where at a distance 510 from the cutting edge tip 310 of approximately 0.003 inches, the web thickness 505 is between 0.0012 inches and 0.0018 inches. Furthermore, a manufacturing process may be utilized to form the cutting edge tip radius 405 between 0.000008 inches and 0.000015 inches. The following are various examples of manufacturing processes for forming the cutting edge profiles within the numerical ranges listed above. For example, referring to FIG. 6, a manufacturing process 600 includes utilizing a grinding process 605 to grind the cutting edge 305 to form the cutting edge angle 410. Alternatively, the grinding process 605 may be utilized to form any of the web thickness profiles 506 described in connection with FIGS. 5A-5C. The grinding process 605 may be performed by a variety of grinding tools, such as an abrasive grinding wheel, for example. Examples of abrasive grinding wheels include silicon carbide, aluminum oxide, and/or diamond coated wheels.

Additionally, a honing process may be used either alone or in combination with the grinding process 605 to form either the cutting edge angle 410 or any of the web thickness profiles 506 shown in FIGS. 5A-5C. Furthermore, in some examples, a stropping process may be used either alone or in combination with either the grinding process or the honing process to form the cutting edge 305. Typically, after the grinding process or honing process 605, a burr remains at the cutting edge tip 310. If this burr is not properly removed, the cutting edge tip 310 will yield and become dull prematurely during a surgical procedure. To remove this burr and to form the cutting edge tip radius 405, an electro-polishing process 610 may be utilized. By precisely controlling various control parameters of the electro-polishing process 610 such as process duration, temperature, voltage, and chemical composition, the cutting edge tip radius 405 may be formed and controlled. Due to the extremely small scale of the cutting edge tip radius 405, the radius can only be accurately measured using specialized equipment such as white light interferometry. Following the electro-polishing process 610, the knife material may be further processed 615 to achieve a Rockwell C hardness value of greater than approximately 47. In some embodiments, the post-manufacturing process 615 may be performed to achieve a Rockwell C hardness value of the knife material between 47 and 53. Examples of post-manufacturing processes include a heat treatment process or a vapor deposition process. In some embodiments, the post-manufacturing process 615 is not needed to achieve a Rockwell C hardness value between 47 and 53. For example, the knife material may be pre-hardened and have a Rockwell C hardness value between 47 and 53 before the grinding or honing process 605 and before the electro-polishing process 610. Alternatively, the post-manufacturing process 615 may be performed after the grinding or honing process 605 but before the electro-polishing process 610.

Figure 7:
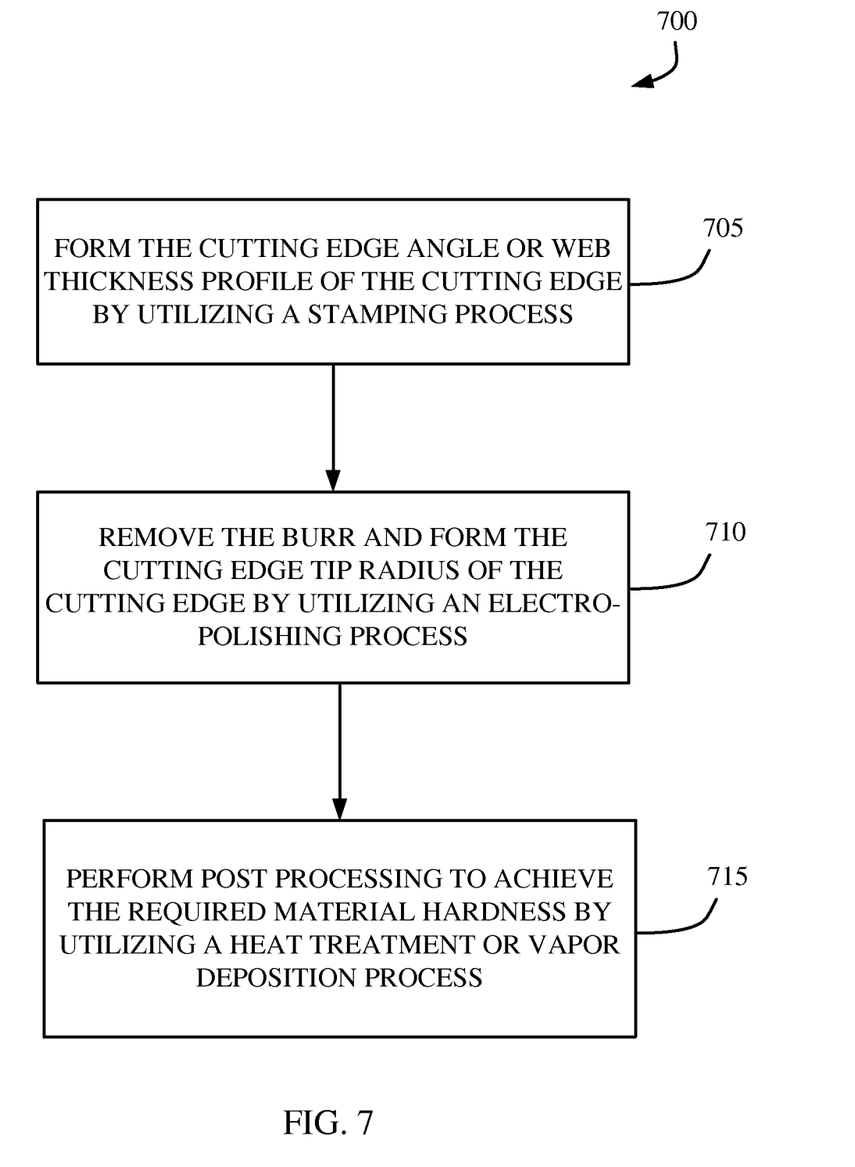
FIG. 7 is a flowchart of a method for forming a surgical knife in accordance with certain embodiments of the present disclosure.

Referring to FIG. 7, an example of a manufacturing process 700 is shown, which may be used to form cutting edge profiles according to various embodiments of the invention. Manufacturing process 700 includes a coining or stamping process 705 to form the cutting edge angle 410.

Alternatively, the stamping process 705 may be utilized to form any of the web thickness profiles 506 shown in FIGS. 5A-5C. Similar to the grinding process 605 described above, typically, after the coining or stamping process 705, a burr remains at the cutting edge tip. To remove this burr and to form the cutting edge tip radius 405, an electro-polishing process 710 may be utilized. By precisely controlling various control parameters of the electro-polishing process such as process duration, temperature, voltage, and chemical composition, the cutting edge tip radius 405 may be formed and controlled. Following the electro-polishing process 710, the knife material may be further processed 715 to achieve a Rockwell C hardness value of greater than approximately 47. In some embodiments, the post-manufacturing process 715 may be performed to achieve a Rockwell C hardness value of the knife material between 47 and 53. Examples of post-manufacturing processes include a heat treatment process or a vapor deposition process. In some embodiments, the post-manufacturing process 715 is not needed to achieve a Rockwell C hardness value between 47 and 53. For example, the knife material may be pre-hardened and have a Rockwell C hardness value between 47 and 53 before the coining or stamping process 705 and before the electro-polishing process 710. Alternatively, the post-manufacturing process 715 may be performed after the coining or stamping process 705 but before the electro-polishing process 710.

Figure 8:
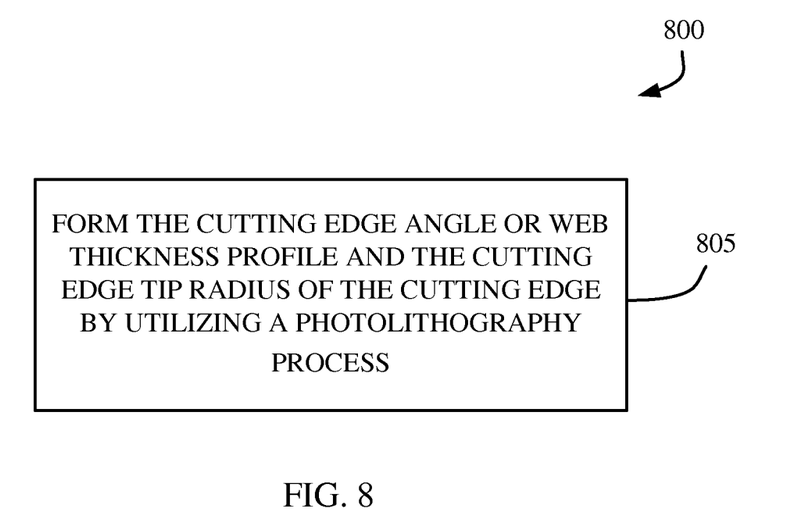
FIG. 8 is a flowchart of a method for forming a surgical knife in accordance with certain embodiments of the present disclosure.

Referring to FIG. 8, a manufacturing process 800 may be used to form cutting edge profiles according to various embodiments of the invention. The manufacturing process 800 includes a photolithography process 805. One particular advantage of the photolithography process 805 is that the knife material may be hardened before the manufacturing process. The photolithography process 805 may used to form the cutting edge angle 410. Additionally, the photolithography process 805 may be used to form any of the web thickness profiles 506 shown in FIGS. 5A-5C. Another advantage of the photolithography process 805 may be that the process does not produce a burr at the cutting edge tip. Therefore, the photolithography process 805 may also be utilized to form the cutting edge tip radius 405 within the ranges previously discussed.

The foregoing description provides examples, and is not intended to limit the scope, applicability or configuration of the various embodiments. Rather, the description and/or figures provide those skilled in the art with an enabling description for implementing various embodiments. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, and devices, may individually or collectively be components of a larger system, wherein other procedures may take precedence over or otherwise modify their application.

The foregoing descriptions of specific embodiments have been presented for purposes of illustration and description. They are not intended to be exhaustive or to limit the invention to the precise forms disclosed, and obviously many modifications and variations are possible in light of the above teaching. The embodiments were chosen and described in order to explain the principles of the various embodiments and its practical application, to thereby enable others skilled in the art to utilize the various embodiments with various modifications as are suited to the particular use contemplated. It is intended that the scope of the various embodiments be defined by the Claims appended hereto and their equivalents.

The invention claimed is:

1. A knife for cutting tissue comprising:
   a double bevel cutting edge comprising a first bevel and a second bevel that each extend along a width direction of the knife, the first and second bevels converging at a tip, wherein a radius of the tip is between 0.000008 inches and 0.000015 inches, and wherein the radius of the tip intersects the first bevel and the second bevel at first and second transition points, respectively; and
   a web thickness profile of the double bevel cutting edge, the web thickness profile defined by a web thickness between the first and second bevels, wherein, starting at the first and the second transition points, the web thickness varies non-linearly as a function of distance from the tip along a direction orthogonal to the double bevel cutting edge, wherein at a distance of 0.003 inches from the tip, the web thickness is between 0.0012 inches and 0.0018 inches.

2. The knife of claim 1, wherein the radius of the tip is between 0.0000092 inches and 0.000014 inches.

3. The knife of claim 1, wherein the radius of the tip is between 0.00001 inches and 0.000013 inches.

4. The knife of claim 1, wherein the radius of the tip is 0.000012 inches.

5. The knife of claim 1, further comprising:
   a cutting edge angle of the cutting edge, wherein the cutting edge angle is between 30 degrees and 34 degrees.

6. The knife of claim 1, further comprising:
   a cutting edge angle of the cutting edge, wherein the cutting edge angle is 32 degrees.

7. The knife of claim 1, further comprising:
   a knife length between 7 inches and 16 inches; and
   a knife width between 0.125 inches and 0.5 inches.

8. The knife of claim 1, wherein within a distance of 0.003 inches from the tip, the knife comprises a material with a Rockwell C hardness between 47 and 53.

9. The knife of claim 8, wherein the material is stainless steel or titanium.

10. The knife of claim 8, wherein the material is coated from a vapor deposition process.

11. The knife of claim 1, wherein the web thickness profile comprises a convex shape or a concave shape.

12. A medical device comprising
   a shaft with a distal end and a proximal end;
   a handle coupled with the proximal end of the shaft, the handle comprising one or more triggers;
   a knife housed within the shaft, the knife comprising:
   a double bevel cutting edge comprising a first bevel and a second bevel that each extend along a width direction of the knife, the first and second bevels converging at a tip, wherein a radius of the tip is between 0.000008 inches and 0.000015 inches, and wherein the radius of the tip intersects the first bevel and the second bevel at first and second transition points, respectively; and
   a web thickness profile of the double bevel cutting edge, the web thickness profile defined by a web thickness between the first and second bevels,
   wherein, starting at the first and the second transition points, the web thickness varies non-linearly as a function of distance from the tip along a direction orthogonal to the double bevel cutting edge, wherein at a distance of 0.003 inches from the tip, the web thickness is between 0.0012 inches and 0.0018 inches, wherein the knife extends from the distal end of the shaft.

13. The medical device of claim 12, further comprising a pair of jaws coupled with the distal end of the shaft, wherein the pair of jaws is configured to hinge open and closed in response to an actuation of at least one of the one or more triggers.

14. The medical device of claim 12, wherein the knife further comprises:

a knife length between 7 inches and 16 inches; and a knife width between 0.125 inches and 0.5 inches.

15. The medical device of claim 12, wherein within a distance of 0.003 inches from the tip of the knife, the knife comprises a material with a Rockwell C hardness between 47 and 53.

16. The medical device of claim 15, wherein the material is stainless steel or titanium, or is coated from a vapor deposition process.

* * * * *